United States Patent [19]

Schröder et al.

[11] 4,453,972
[45] Jun. 12, 1984

[54] PHENOXY PYRIDINE DERIVATIVES AND HERBICIDAL COMPOSITIONS CONTAINING SAME

[75] Inventors: Ludwig Schröder, Ingelheim am Rhein; Werner Stransky, Gau-Algesheim; Rudolf Mengel; Gerbert Linden, both of Ingelheim am Rhein, all of Fed. Rep. of Germany

[73] Assignee: Celamerck GmbH & Co., KG, Ingelheim am Rhein, Fed. Rep. of Germany

[21] Appl. No.: 460,471

[22] Filed: Jan. 24, 1983

Related U.S. Application Data

[63] Continuation of Ser. No. 321,445, Nov. 16, 1981.

[30] Foreign Application Priority Data

Nov. 28, 1980 [DE] Fed. Rep. of Germany ....... 3044856

[51] Int. Cl.³ .................... A01N 43/40; C07D 213/63
[52] U.S. Cl. .......................................... 71/94; 546/302
[58] Field of Search ............................ 546/302; 71/94

[56] References Cited

U.S. PATENT DOCUMENTS

| | | | |
|---|---|---|---|
| 3,429,689 | 2/1969 | Duerr et al. ............................ | 71/94 |
| 4,030,910 | 6/1977 | Johnston ................................ | 71/94 |
| 4,105,435 | 8/1978 | Nishiyama et al. ................... | 546/302 |
| 4,235,621 | 11/1980 | Nishiyama et al. ..................... | 71/94 |
| 4,302,242 | 11/1981 | Cartwright ........................ | 546/302 |

*Primary Examiner*—Jane T. Fan

*Attorney, Agent, or Firm*—Hammond & Littell, Weissenberger & Dippert

[57] ABSTRACT

This invention relates to novel pyridine derivatives of the formula

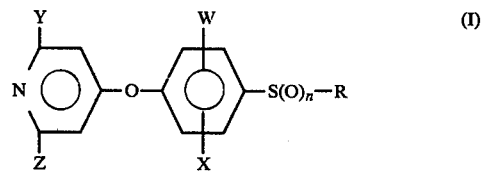

wherein
n is 0, 1, or 2;
R is an alkyl radical having from 1 to 4 carbon atoms, unsubstituted or substituted by one or more fluorine or chlorine atoms, alkenyl radical having from 2 to 4 carbon atoms, a benzyl radical, or a chlorine-substituted or methyl-substituted benzyl radical;
W and X, which may be identical or different, are each a hydrogen, chlorine, fluorine, bromine, or iodine atom or alkyl having from 1 to 4 carbon atoms;
Y is a hydrogen, chlorine, fluorine, or bromine atom or alkyl having from 1 to 4 carbon atoms; and
Z is a chlorine or fluorine atom.

This invention also relates to the preparation of the compounds of Formula I and their use as active ingredients in biocidal, especially, herbicidal, compositions.

8 Claims, No Drawings

PHENOXY PYRIDINE DERIVATIVES AND HERBICIDAL COMPOSITIONS CONTAINING SAME

This application is a continuation of co-pending U.S. patent application Ser. No. 321,445, filed Nov. 16, 1981.

This invention relates to novel pyridine derivatives of the formula

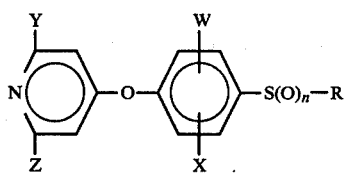

wherein
n is 0, 1, or 2;
R is an alkyl radical having from 1 to 4 carbon atoms, unsubstituted or substituted by one or more fluorine or chlorine atoms, an alkenyl radical having from 2 to 4 carbon atoms, a benzyl radical, or a chlorine-substituted or methyl-substituted benzyl radical;
W and X, which may be identical or different, are each a hydrogen, chlorine, fluorine, bromine, or iodine atom or an alkyl having from 1 to 4 carbon atoms;
Y is a hydrogen, chlorine, fluorine, or bromine atom or an alkyl having 1 to 4 carbon atoms; and
Z is a chlorine or fluorine atom.

This invention also relates to the preparation of the compounds of Formula I and their use as active ingredients in biocidal, especially herbicidal, compositions.

In a preferred embodiment of the invention, R is methyl or halogenated methyl, for example, CH$_2$Cl or CF$_3$; W, X, and Y, which can be identical or different, are each hydrogen, methyl, or chlorine; and Z is chlorine. If the aliphatic radicals have 3 or 4 carbon atoms, they can be linear or branched.

German Offenlegungsschrift No. 1,542,736 discloses aryloxy-substituted pyridines which correspond to the general formula

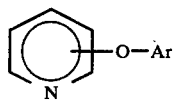

wherein Ar represents an optionally substituted aryl group. These compounds, which do not have additional substituents in the pyridine ring and which in particular encompass, for example, the compound

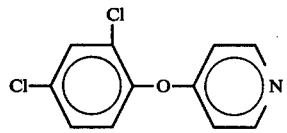

do not have a sufficiently satisfactory action.

In contradistinction, the compounds according to the invention are distinguished by a powerful action against numerous weeds, especially dicotyledonous weeds, including, for example, weeds which are difficult to control, such as Galium aparine and Veronica hederifolia. They are preferably used for pre-emergence application. An important practical aspect with regard to utility of the compounds of Formula I is the capability of filling the gap of numerous otherwise very well-proven commercial products by employing the novel active ingredients conjointly with these. Examples of partners in combinations of this type are chlorotoluron and related urea derivatives, terbutryn and related triazine derivatives, trifluraline and related derivatives, alachlor, and dimethachlor.

The novel compounds of Formula I are prepared in a manner known per se. To do so, a pyridine derivative of the formula

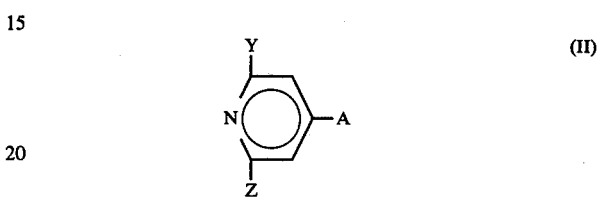

wherein Y and Z are as defined above and A is halogen, especially chlorine or fluorine, or NO$_2$, is reacted with a phenol or phenolate of the formula

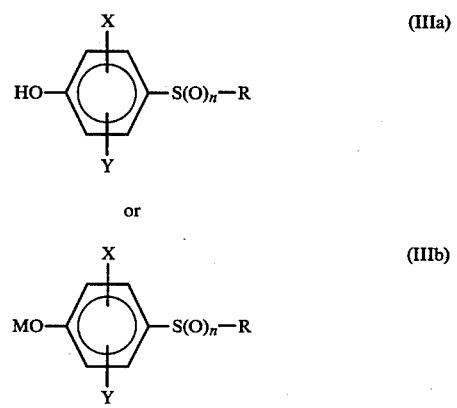

wherein R, X, Y, and n are as defined above and M is one equivalent of a cation, preferably Na$^+$, K$^+$, or $\frac{1}{2}$ Ca$^{++}$, and, if desired, those reaction products in which n is 0 or 1 are oxidized to the higher oxidation levels (with n=1 or 2, respectively).

The reaction of the compounds of Formulas II and IIIa or IIIb is carried out at temperatures between ambient temperature and about 160° C. Preferably, the reaction is carried out in polar solvents, such as acetone, butan-2-one, acetonitrile, dimethylformamide, or dimethylsulphoxide, at the boiling point of the reaction mixture. In carrying out the reaction of the phenols, acid acceptors, for example, alkali metal carbonates, such as Na$_2$CO$_3$ or K$_2$CO$_3$, or alkali metal hydroxides or alkaline earth metal hydroxides, such as NaOH, KOH, or Ca(OH)$_2$, are added. To achieve a favorable yield, it can be advantageous to employ the phenol or its salts and/or the acid acceptor in excess.

To oxidize the mercapto compounds to the corresponding sulphinyl and sulphonyl compounds, or to oxidize the sulphinyl compounds to the sulphonyl compounds, the customary oxidation agents for this reaction are employed. For the oxidation of the thioethers to the sulphinyl compounds, nitric acid, one equivalent of hydrogen peroxide, dinitrogen tetroxide, or bromine, chlorine, or iodine may be mentioned. For the oxidation of the thioethers or the sulphinyl compounds to the sulphonyl compounds, appropriately increased amounts of hydrogen peroxide, potassium hydrogen persulphate, or potassium permanganate are used.

The starting materials of the compounds of Formulas II, IIIa, and IIIb are known or can be obtained analogously to the known compounds.

The following examples are intended to illustrate the preparation of compounds of the invention and are not to be construed as limiting the invention thereto.

EXAMPLES

EXAMPLE 1

2-Chloro-4-(3-methyl-4-methylmercapto-phenoxy)-pyridine

A solution of 17 gm (0.1 mol) of 3-methyl-4-methylmercaptophenol and 15.9 gm (0.1 mol) of 2-chloro-4-nitropyridine in 150 ml of acetonitrile was mixed with 13.8 gm (0.1 mol) of $K_2CO_3$ and stirred for 3 hours under reflux. It was then cooled and poured into 300 ml of water. The oil which separated out was separated off and taken up in methylene chloride, and the solution was washed with dilute sodium hydroxide solution and with water. The organic solution was then dried over $Na_2SO_4$ and concentrated by evaporation. The oil which remained was crystallized from hexane.

Yield: 23 gm (86% of theory).
M.p.: 45°–46° C.
Analysis: $C_{13}H_{12}ClNOS$ (265.76) Calc., C 58.75, H 4.55, N 5.27; Found: C 59.02, H 4.60, N 4.98.

EXAMPLE 2

2-Chloro-4-(2,5-dichloro-4-methylsulphinyl-phenoxy)-pyridine

An amount of 32.6 gm (0.1 mol) of 2-chloro-4-(2,5-dichloro-4-methylmercaptophenoxy)-pyridine, prepared analogously to Example 1, was suspended in 100 ml of glacial acetic acid. The mixture was warmed to 45° to 50° C., and 11 ml (0.11 mol) of 30% $H_2O_2$ were added dropwise at such a rate that the internal temperature did not exceed 50° C. The mixture was then stirred for 3 hours at 50° C., after which it was cooled and poured into 300 ml of water. The batch was stirred until crystallization was complete, and the product was recovered by suction filtration, washed with water, dried, and recrystallized from ethyl acetate.

Yield: 20.2 gm (60% of theory).
M.p.: 117°–120° C.
Analysis: $C_{12}H_8Cl_3NO_2S$ (336.63) Calc.: C 42.8, H 2.39, N 4.16; Found: C 42.84, H 2.54, N 4.08.

EXAMPLE 3

2-Chloro-4-(2,5-dichloro-4-methylsulphonyl-phenoxy)-pyridine

An amount of 32.06 gm (0.1 mol) of 2-chloro-4-(2,5-dichloro-4-methylmercaptophenoxy)-pyridine, prepared analogously to Example 1, was suspended in 100 ml of glacial acetic acid. The mixture was warmed to 80° C., with stirring, and 22 ml (0.22 mol) of 30% $H_2O_2$ were added dropwise at a rate such that the internal temperature did not exceed 90° C. The mixture was then stirred for a further 4 hours at the same temperature. Thereafter it was cooled and poured onto 300 ml of water. The precipitate formed was recovered by filtration, washed with water, dried, and recrystallized from ethyl acetate.

Yield: 28.6 gm (81% of theory).
M.p.: 155°–157° C.
Analysis: $C_{12}H_8Cl_3NO_3S$ (352.63) Calc.: C 40.85, H 2.29, N 3.96; Found: C 40.97, H 2.48, N 4.08.

EXAMPLE 4

2-Chloro-6-methyl-4-(2,5-dichloro-4-methylmercapto-phenoxy)-pyridine

A solution of 25.5 gm (0.1 mol) of potassium 2,5-dichloro-4-methylmercapto-phenolate and 16.2 gm (0.1 mol) of 2,4-dichloro-6-methyl-pyridine in 100 ml of dimethylformamide was heated under reflux for 5 hours. It was then cooled and poured into 300 ml of water. The precipitate which separated out was recovered by suction filtration, washed with water, and recrystallized from isopropanol.

Yield: 13 gm (39% of theory).
M.p.: 145°–148° C.
Analysis: $C_{13}H_{10}Cl_3NOS$ (334.65) Calc.: C 46.65, H 3.01, N 4.19; Found: C 46.98, H 3.17, N 4.02.

EXAMPLE 5

2,6-Dichloro-4-(2,5-dichloro-4-methylmercapto-phenoxy)-pyridine (a) 2,6-Dichloro-4-nitropyridine A solution of 20.9 gm (0.1 mol) of 2,6-dichloro-4-nitropyridine-1-oxide (J. Chem. Soc. B 1967, 1235) in 100 ml of ethylene chloride was heated to boiling and then 27.5 gm (0.2 mol) of phosphorus trichloride were added. The solution obtained was stirred for a further 8 hours under reflux and was then concentrated by evaporation in vacuo. The oily residue which remained was poured into ice water. The crystalline residue formed was recovered by suction filtration and washed neutral with water.

Yield: 17.5 gm (91% of theory).
M.p.: 98°–99° C.
Analysis: $C_5H_2Cl_2N_2O_2$ (193) Calc.: C 31.11, H 1.04, N 14.52; Found: C 31.31, H 1.30, N 14.38.

(b) 2,6-Dichloro-4-(2,5-dichloro-4-methylmercapto-phenoxy)-pyridine

Quantities of 19.3 gm (0.1 mol) of 2,6-dichloro-4-nitropyridine and 23.1 gm (0.11 mol) of 2,5-dichloro-4-methylmercaptophenol were dissolved in 100 ml of acetone, 13.8 gm (0.1 mol) of $K_2CO_3$ were added, and the resulting mixture was stirred for 3 hours under reflux. It was then stirred into 500 ml of water, and the precipitate formed was recovered by suction filtration.

Yield: 32.5 gm (91.5% of theory).
M.p.: 144°–146° C.
Analysis: $C_{12}H_7Cl_4NOS$ (355.08) Calc.: C 40.59 H 1.99, N 3.95; Found: C 40.78 H 2.30, N 3.85.

EXAMPLE 6

2-Fluoro-6-methyl-4-(2,5-dichloro-4-methylmercapto-phenoxy)-pyridine

Amounts of 12.9 gm (0.1 mol) of 2,4-difluoro-6-methylpyridine, 20.7 gm (0.1 mol) of 2,5-dichloro-4-methylmercaptophenol, and 13.8 gm (0.1 mol) of potassium carbonate in 100 ml of dimethylformamide were stirred for 10 hours at 100° C. The resulting solution was then poured onto 500 ml of ice water, and the precipitate formed was recovered by suction filtration and washed with water. It was then taken up in methylene chloride, and this solution was dried over sodium sulphate and evaporated down. The oil obtained was purified over a silica gel column (ethylene chloride as the eluant) and 16.3 gm (57% of theory) of the desired ether were obtained.

M.p.: 93°–95° C.

By use of procedures analogous to those described above, the following compounds were prepared:

EXAMPLE 7

2,6-Difluoro-4-(2,5-dichloro-4-methylmercaptophenoxy)-pyridine (melting point: 96°–98° C.).

EXAMPLE 8

2,6-Difluoro-4-(2,5-dichloro-4-methylsulphinylphenoxy)-pyridine (melting point: 138°–140° C.).

EXAMPLE 9

2-Fluoro-6-methyl-4-(2,5-dichloro-4-methylmercaptophenoxy)-pyridine (melting point: 93°–95° C.).

The compounds represented in the table below were also prepared using procedures analogous to those set forth in Examples 1 to 6.

The action of certain compounds of Formula I, the specific preparation of which is discussed in the Examples above, was tested in a greenhouse experiment using 4 kg/ha (preemergence values). The compound 4-(2,4-dichlorophenoxy)pyridine (Compound A), disclosed in German Offenlegungsschrift No. 1,543,736, was used for the purpose of comparison. Assessment of the action of the compounds tested was reflected by a nine-stage rating scale where 1=100% effective and 9=no effect. The results of the testing were as follows:

TABLE II

| Active Substance | Effect on *Sinapis alba* | Effect on *Lycopersicum esculentum* |
|---|---|---|
| Compound A* | 9 | 9 |
| Example 1 | 1 | 1 |
| Example 3 | 1 | 1 |
| Example 22 | 2 | 1 |
| Example 30 | 1 | 1 |
| Example 39 | 1 | 1 |

*Comparison

As indicated above, the compounds of Formula I are effective biocidal, particularly herbicidal, active ingredients. The good activity of the compounds is coupled with good tolerance in numerous crops, thereby making

TABLE I

Compounds of the formula $$\text{Cl-pyridine(Y)-O-phenyl(W,X)-S(O)}_n\text{-R}$$

| Example No. | Y | W | X | n | R | M.p. or (B.p./mbar) |
|---|---|---|---|---|---|---|
| 10 | H | H | H | 0 | CH$_3$ | 74–65° C. |
| 11 | H | H | H | 1 | CH$_3$ | (199–201° C./0.02) |
| 12 | H | H | H | 2 | CH$_3$ | 120–122° C. |
| 13 | H | 2-CH$_3$ | H | 0 | CH$_3$ | (155–160° C./0.01) |
| 14 | H | 2-CH(CH$_3$)(C$_2$H$_5$) | H | 0 | CH$_3$ | (175–180° C./0.01) |
| 15 | H | 2-Cl | 5-Cl | 0 | CH$_3$ | 108–110° C. |
| 16 | H | 3-Cl | 5-Cl | 1 | CH$_3$ | 83–86° C. |
| 17 | H | 3-Cl | 5-Cl | 2 | CH$_3$ | 118–121° C. |
| 18 | H | 3-Cl | 5-Cl | 0 | CH$_2$—C$_6$H$_5$ | 72–76° C. |
| 19 | H | 3-Cl | 5-Cl | 1 | CH$_2$—C$_6$H$_5$ | 110–113° C. |
| 20 | H | 3-Cl | 5-Cl | 2 | CH$_2$C$_6$H$_5$ | 166–169° C. |
| 21 | H | 3-Cl | 5-Cl | 0 | CH$_2$—CH=CH$_2$ | (193–196° C./0.04) |
| 22 | H | 3-Cl | H | 0 | CH$_3$ | 82–84° C. |
| 23 | H | 3-Cl | H | 1 | CH$_3$ | 85–88° C. |
| 24 | H | 3-Cl | H | 2 | CH$_3$ | 125–129° C. |
| 25 | H | 3-CH$_3$ | 5-CH$_3$ | 0 | CH$_3$ | (192–196° C./0.08) |
| 26 | CH$_3$ | H | H | 0 | CH$_3$ | 68–72° C. |
| 27 | CH$_3$ | H | H | 0 | CH$_3$ | (180–185° C./0.002) |
| 28 | CH$_3$ | 3-Cl | H | 0 | CH$_3$ | 109–111° C. |
| 29 | CH$_3$ | 3-Cl | H | 1 | CH$_3$ | 129–130° C. |
| 30 | CH$_3$ | 3-Cl | H | 2 | CH$_3$ | 118–120° C. |
| 31 | CH$_3$ | H | H | 2 | CH$_3$ | 119–121° C. |
| 32 | CH$_3$ | 3-Cl | H | 0 | C$_4$H$_9$ | 81–84° C. |
| 33 | CH$_3$ | 2-Cl | 5-Cl | 1 | CH$_3$ | 144–146° C. |
| 34 | CH$_3$ | 2-Cl | 5-Cl | 2 | CH$_3$ | 164–167° C. |
| 35 | CH$_3$ | 3-Cl | 5-Cl | 0 | CH$_3$ | 121–123° C. |
| 36 | CH$_3$ | 3-Cl | 5-Cl | 0 | CH$_2$—CH=CH$_2$ | 103–105° C. |
| 37 | Cl | H | H | 0 | CH$_3$ | 86–88° C. |
| 38 | Cl | 2-Cl | 5-Cl | 1 | CH$_3$ | 175–178° C. |
| 39 | Cl | 2-Cl | 5-Cl | 2 | CH$_3$ | 204–206° C. |
| 40 | Cl | 2-Cl | 5-Cl | 0 | CH$_2$Cl | oil |
| 41 | Cl | 2-Cl | 5-Cl | 0 | CF$_3$ | oil | selective use possible. More particularly, the compounds of the invention are useful for pre-emergence and post-emergence weed control in agricultural fields, such as oats, wheat, barley, potato, soybean, cotton, and pea fields. Examples of weeds which can be controlled with the aid of the compounds of Formula I include wild mustard, amaranth, goosefoot, chamomile, slender foxtail, and the like.

For combination herbicidal compositions, especially for post-emergence treatment, the following substances are particularly suitable:
1. Growth-factor herbicides, such as 2,4-DP, MCPA and CMPP;
2. Contact herbicides, such as ioxynil, bromoxynil, bentazon, bromphenoxin, and dinoterb; and
3. Grass herbicides, such as isoproturon and diclofop-methyl.

For use in plant protection, the compounds of Formula I are incorporated as active ingredients into conventional herbicidal compositions, that is, compositions consisting essentially of inert liquid or solid carrier and an effective herbicidal amount of the active ingredient, such as emulsion concentrates, wettable powders, granulates, dusting powders, or the like. For example, the active ingredient content of emulsion concentrates or wettable powders, which are diluted with water prior to dissemination, is from about 10 to 95% by weight. In the case of dusting powders and granulates, which are disseminated without dilution, the active ingredient may range from about 0.2 to 20% by weight, preferably from about 0.5 to 3% by weight.

With regard to the actual amount of active ingredient employed as herbicides, amounts of from about 0.005 to 2 kg/ha, preferably from about 0.1 to 1 kg/ha, are employed, dependent upon the substance used and on the weed to be controlled. In combination with other herbicides, even smaller amounts (down to about 0.05 kg/ha) of the compounds according to the invention suffice.

The following examples illustrate a few herbicidal compositions containing a compound of Formula I as the active ingredient:

EXAMPLE 42

| Wettable Powder | |
|---|---|
| Component | % by Weight |
| Compound of Formula I (as active ingredient) | 25 |
| Kaolin | 55 |
| Colloidal silica | 10 |
| Calcium ligninsulfonate (as dispersant) | 9 |
| Sodium tetrapropylene-benzene-sulfonate (as wetting agent) | 1 |

Prior to use, the powder is diluted with water to form a sprayable suspension containing from about 0.05 to 0.5% by weight of the active ingredient.

EXAMPLE 43

| Wettable Powder | |
|---|---|
| Component | % by Weight |
| Compound of Formula I | 80 |
| Calcium ligninsulfonate | 8 |
| Colloidal silica | 5 |
| Sodium sulfate | 5 |
| Sodium diisobutylnaphthalenesulfonate | 2 |

This powder was diluted in the same manner as the powder of Example 42.

EXAMPLE 44

| Emulsion Concentrate | |
|---|---|
| Component | % by Weight |
| Compound of Formula I | 40 |
| SHELLSOL A (a mixture of liquid, high-boiling aromatic hydrocarbon solvents) | 25 |
| N—Methylpyrrolidone | 25 |
| EMULSOGEN I 40 (anionic emulsifier) | 10 |

Prior to use, the emulsion concentrate is diluted with water to form a sprayable aqueous emulsion containing from about 0.05 to 5% by weight of the active ingredient.

It is contemplated that any compound of Formula I, or even a combination thereof, could be used as active ingredient in the compositions of Examples 42 to 44. It is also contemplated that the amount of active ingredient in these illustrative examples may be varied to achieve the effective range set forth above. Moreover, the amount and nature of the inert carrier ingredients may be varied to meet particular requirements.

The preceding specific embodiments are illustrative of the practice of the invention. It is to be understood, however, that other expedients known to those skilled in the art or disclosed herein, may be employed without departing from the spirit of the invention or the scope of the appended claims.

We claim:
1. A compound of the formula

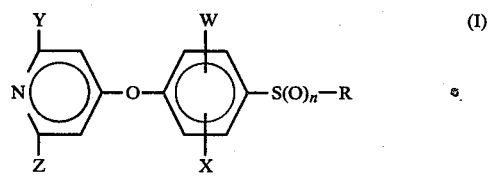

wherein
n is 0, 1, or 2;
R is an alkyl radical having from 1 to 4 carbon atoms, unsubstituted or substituted by one or more fluorine or chlorine atoms, alkenyl radical having from 2 to 4 carbon atoms, a benzyl radical, or a chlorine-substituted or methyl-substituted benzyl radical;
W and X, which may be identical or different, are each a hydrogen, chlorine, fluorine, bromine, or iodine atom or alkyl having from 1 to 4 carbon atoms;
Y is a hydrogen, chlorine, fluorine, or bromine atom or alkyl having from 1 to 4 carbon atoms; and
Z is a chlorine or fluorine atom.

2. A compound of claim 1, wherein R is methyl or halogenated methyl and W, X, and Y, which may be identical or different, are each hydrogen, chlorine, or methyl.

3. A herbicidal composition comprising an effective herbicidal amount of a compound of claim 1 as active ingredient and an inert liquid or solid carrier.

4. A method of controlling weeds which comprises administering to an area in need thereof an effective amount of a compound of claim 1.

5. A herbicidal composition comprising an effective herbicidal amount of a compound of claim 2 as active ingredient and an inert liquid or solid carrier.

6. A method of killing weeds which comprises contacting them with a herbicidal composition of claim 3.

7. A method of killing weeds which comprises contacting them with a herbicidal composition of claim 5.

8. A method of controlling weeds which comprises administering to an area in need thereof an effective amount of a compound of claim 2.

* * * * *